(12) United States Patent
Cohen

(10) Patent No.: US 8,507,853 B2
(45) Date of Patent: Aug. 13, 2013

(54) METHOD AND SYSTEM FOR DETERMINING DEPTH PROFILING

(75) Inventor: Hagai Cohen, Rehovot (IL)

(73) Assignee: Yeda Research and Development Company Ltd., Rehovot (IL)

( * ) Notice: Subject to any disclaimer, the term of this patent is extended or adjusted under 35 U.S.C. 154(b) by 143 days.

(21) Appl. No.: 13/124,224

(22) PCT Filed: Oct. 22, 2009

(86) PCT No.: PCT/IL2009/000991
§ 371 (c)(1),
(2), (4) Date: May 16, 2011

(87) PCT Pub. No.: WO2010/046896
PCT Pub. Date: Apr. 29, 2010

(65) Prior Publication Data
US 2011/0210246 A1    Sep. 1, 2011

Related U.S. Application Data

(60) Provisional application No. 61/107,387, filed on Oct. 22, 2008.

(51) Int. Cl.
*H01J 37/26* (2006.01)
(52) U.S. Cl.
CPC .................................... *H01J 37/26* (2013.01)
USPC ............. 250/305; 250/307; 250/306; 378/83; 378/88
(58) Field of Classification Search
USPC ..................... 250/307, 306, 305; 378/83, 85, 378/88
See application file for complete search history.

(56) References Cited

U.S. PATENT DOCUMENTS 7,148,478 B2 * 12/2006 Cohen et al. ................. 250/306
2002/0020814 A1   2/2002 Cohen et al.

OTHER PUBLICATIONS

Briggs et al., "Practical Surface Analysis," 1990, pp. 143-199, 248-251, 496-498, vol. 1, 2$^{nd}$ Ed., Wiley: New York.
Cumpson et al., "Elastic Scattering Corrections in AES and XPS, II. Estimating Attenuation Lengths and Conditions Required for their Valid Use in Overlayer/Substrate Experiments," *Surface and Interface Analysis*, 1997, pp. 430-446, vol. 25.
Hirose et al., "Photoelectron Spectroscopy Studies of $SiO_2$/Si Interfaces," *Progress in Surface Science*, 2007, p. 3-54, vol. 82.
Jablonski et al., "Elastic-electron-scattering effects on angular distributions in x-Ray-photoelectron spectroscopy," *Physical Review B*, Aug. 1994, pp. 4739-4748, vol. 50, No. 7.
Tyler et al., "Regularization: a Stable and Accurate Method for Generating Depth Profiles from Angle-Dependent XPS Data," *Surface and Interface Analysis*, 1989, pp. 443-450, vol. 14.

(Continued)

*Primary Examiner* — Kiet T Nguyen
(74) *Attorney, Agent, or Firm* — Oliff & Berridge, PLC

(57) ABSTRACT

The present invention relates to a novel system and method for the determination of depth profiling with improved accuracy and reliability. The method comprises obtaining spectroscopic data from the sample while under at least two different electrical conditions of the sample, the spectroscopic data comprising a signal of charged particles emitted from the sample, and being indicative of a change in amplitude, spectral position and spectral shape of the signal from the sample while under different electrical conditions of the sample, the change being indicative of the compositional profile and spatial distribution for at least one chemical element in the sample along a direction through the sample.

14 Claims, 5 Drawing Sheets

(56) References Cited

OTHER PUBLICATIONS

Tougaard, "Quantitative Analysis of the Inelastic Background in Surface Electron Spectroscopy," *Surface and Interface Analysis*, 1988, pp. 453-472, vol. 11.

Tougaard, "Surface nanostructure determination by x-Ray photoemission spectroscopy peak shape analysis," *J. Vac. Sci. Technol. A.*, 1996, pp. 1415-1423, vol. 14, No. 3.

Budrevich et al., "Nitrogen depth profiling in thin oxynitride layers on silicon," *Surface and Interface Analysis*, 2006, pp. 267-271, vol. 38.

Rozenblat et al., "Electrical depth profiling in thin SiON layers," *Applied Physics Letters*, 2009, pp. 53116-1-53116-3, vol. 94.

Chattopadhyay et al., "Thermal and viscoelastic properties of polyurethane-imide/clay hybrid coatings," *Polymer Degradation and Stability*, 2006, pp. 1837-1849, vol. 91.

\* cited by examiner

METHOD AND SYSTEM FOR DETERMINING DEPTH PROFILING

FIELD OF THE INVENTION

This invention is in the field of depth profiling techniques and relates to a method and system for mapping the material distribution within a structure.

REFERENCES

The following references are considered to be pertinent for the purpose of understanding the background of the present invention:
1. Practical Surface Analysis Vol. 1, 2nd Edn., Briggs, D. & Seah, M. P. (Eds.), Wiley, New York, 1990;
2. P. J. Cumpson, M. P. Seah, Surf. Interf. Anal. 25, 430 (1997);
3. K. Hirose, H. Nohira, K. Azuma, T. Hattori, Progress in Surface Science 82, 3-54, (2007);
4. A. Jablonski, C. J. Powell, Phys. Rev. B 50, 4739 (1994);
5. Tyler, B. J., Castner, D. G. & Ratner, B. D. Regularization—A stable and accurate method for generating depth profiles from angle-dependent XPS data. Surf. Interf. Anal. 14, 443-450 (1989).
6. Tougaard, S. Quantitative analysis of the inelastic background in surface electron spectroscopy. Surf. Interf. Anal. 11, 453-472 (1988); S. Tougaard, J. Vac. Sci. Technol. A 14, 1415 (1996).
7. A. Budrevich, A. Gladkikh, E. Kaganer, and M. Sokolovsky, Surf. Interface Anal. 38, 267 (2005).

BACKGROUND OF THE INVENTION

Depth profiling can be used for determining the spatial distribution of chemical elements in a sample, along the direction perpendicular to the sample's surface. Such information has great importance in various research and technological fields, particularly, for example, for inspection in VLSI wafer production lines.

Characterization methods that can determine compositional profiles across nanometer thick layered structures are of utmost importance to ultrathin gate oxide based devices, in particular, and to the current microelectronic science and industry in general. Such an example is the process dependent nitrogen distribution in silicon oxynitride (SiON) films, where nitrogen atoms are intentionally added to the $SiO_2$ network to obtain improved diffusion barrier properties and enhanced immunity from hot carrier damage.

As depth profiling probes, secondary ion mass spectroscopy (SIMS) and Ar milling in core electron spectroscopy are commonly used. However, these destructive tools frequently induce major profile distortions. High depth profiling accuracy was demonstrated with nondestructive angle resolved x-ray photoelectron spectroscopy (ARXPS) of thin structures up to about 10 nm thick. ARXPS requires relatively long measurements and careful interpretation of a non-unique solution associated with an ill-defined inverse problem. Its analysis is largely improved by considering the role of elastic scattering events, and considerable progress can be achieved by evaluating also the background and satellite line intensities.

An alternative approach, which does not rely on the analysis of line intensities, has been proposed for nondestructive profiling: controlled surface charging (CSC). CSC extracts spatial information from the energy axis of the spectrum while creating potential gradients across the studied volume. Extension of CSC to consistent chemically resolved electrical measurements (CREM) has been demonstrated. CREM and CSC are both non-contact methods, proposing unique capabilities, down to atomic scale resolution of the electrostatic potential.

GENERAL DESCRIPTION

The present invention provides a novel technique for the determination of depth profiling with improved accuracy and reliability. The invention utilizes processing and analyzing of measurement results of two or more spectroscopic measurements with at least one condition being different in these measurements, and construction of a single, unified solution for a material distribution through a sample. The determination of the material distribution through the sample can be used for examination/inspection of a sample, typically multilayer or multiple materials containing sample. The sample may for example be a heterostructure.

Therefore, there is provided a method for examining a sample, the method comprising: obtaining spectroscopic data from the sample while under at least two different electrical conditions of the sample, said spectroscopic data comprising a signal of charged particles emitted from the sample, and being indicative of a change in amplitude, spectral position and spectral shape of the signal from the sample with a change in the electrical condition of the sample, said change being indicative of the compositional profile and spatial distribution for at least one chemical element in the sample along a direction through the sample.

The present invention takes advantages of the principles of the spectroscopic technique utilizing measurements taken in at least two different surface charge states of a sample (e.g. CSC), and further utilizes a novel multi-parameter measurements and analysis. The invention utilizes spectroscopic data indicative of different, independent from one another, all being depth-dependent, parameters of the sample. More specifically, the invention utilizes measurement of a change in the amplitude, in the position (spectral shift) and in the shape of the photoelectron signal from the sample, while the sample is under different electrical conditions, e.g. different surface charge conditions (obtained e.g. by varying the bias voltage applied to the sample and/or irradiating the sample by electron flux). Such spectroscopic data includes first spectroscopic data being quantified-type data (amplitude change of a photoelectron signal from the sample) and being thus indicative of a material compositional profile of the sample along a direction perpendicular to a surface of the sample (i.e. depth direction); and second spectroscopic data being indicative of spectral line shifts and shape distortion and thus indicative of spatial distribution of chemical elements in the sample along said direction. This technique utilizes detailed analysis of the line position and shape distortions and combines the results of this electrical analysis with the amplitude change (intensity integral values) information. It should be understood that the known depth profiling techniques use either the line intensity changes, or the peak (line) shift. The present invention utilizes a combination of these two analyses and also utilizes the analysis of line shape distortion (change), caused by a change in the electrical condition of the sample. The technique of the invention utilizes the different type measures while under full correlation of the electrical effect based measurement (spectral shift and shape distortion e.g. energy dependence of the electron attenuation length) with the (integral) line-intensity measurement (namely, spectral effect). This provides significant improvement of the depth profiling capabilities, first in its resolution, and even more importantly, in the capability to identify 'complicated' structures, e.g. with poor chemical contrast and/or broad and interfering compositional distribution functions. The marked improvement in extracting such complicated profiles stems from the complementarity of the electrical and the signal intensity data: both are depth dependent, however the former affects the energy (on the horizontal axis of the spectrum) and the latter affects the intensity (namely, the vertical axis of the spectrum, i.e. the amplitude change through the measured spectrum).

It should be noted that the invention utilizes two or more measurement sessions, each for measuring at least two different parameters of the sample (e.g. signal intensity data and spectral shift and line shape data). The second spectroscopic data may be obtained when the sample is under different surface charge conditions, in other words the measurement session may utilize only measurements under different surface charge conditions (e.g. based on the principles of CSC or CREM measurements), or a combination of such measurements with one or more ARXPS measurements.

In some embodiments, the first and second spectroscopic data are obtained while carrying out the electrical effect based measurements. The second spectroscopic data (corresponding to electrical effect) is indicative of attenuation of the photoelectron signal from the sample, being a function of a material composition and spatial distribution of the sample. In some embodiments, the first spectroscopic data (intensity values) can be obtained while using ARXPS/ARES measurements. The technique of the present invention provides important advantages over the known depth profiling techniques. It is non-destructive and yet allows particularly high spatial resolution for the material distribution (down to ~1 Å). It should be understood that the technique of the present invention not only allows for locating an interface between different material layers, but also provides for profiling a certain material distribution across a layer containing this material.

The technique of the present invention enables characterization of samples (e.g. heterostructures) with poor chemical contrast. In a specific and non-limiting example, the internal structure of SiON layers, where the chemical contrast across the layer may be rather poor, can be characterized by using the technique of the present invention. The measured data is in this case indicative of the inhomogeneity of nitrogen across the structure.

More specifically, the internal structure of SiON films is extracted electrically, demonstrating an efficient, non-contact, non-destructive technique for depth compositional analysis in gate oxides. The electrical data, obtained using X-ray photoelectron spectroscopy (XPS), is compared with independent time of flight secondary ion mass spectroscopy (SIMS) and angle resolved XPS (ARXPS) data. The present invention enables to reveal inhomogeneity in the internal nitrogen distribution i.e. an inhomogeneous composition with significant nitrogen enrichment at the top of the oxide layer. The method of the present invention thus enables fast, nondestructive identification of the major compositional features in modern microelectronic devices, and further, provides fine details of the elemental distribution functions.

In some embodiments, analyzing the spectroscopic data comprises fitting the measured data to corresponding theoretical data. It should be understood that the general information about the material distribution in the sample might be known, or could be obtained carrying out either one of the known spectral techniques.

In some embodiments, the first and second spectroscopic data are obtained by (i) exciting the sample with high energy radiation to cause emission of internal charged particles from the sample; (ii) establishing certain electrical condition of the sample (e.g. supplying electrical power to a circuit formed by the sample and any added component connected to the sample) by carrying out at least one of the following: irradiating the sample by (low energy) charged particles, subjecting the sample to an external field, possibly supplying a bias voltage to the back contact of the sample, and optionally supplying or varying electromagnetic irradiation onto the sample; (iii) during the power supply to the sample, measuring the emitted charged particles versus their energy.

In some embodiments, the first and second spectroscopic data are obtained by carrying out at least one of the following: (a) controlled surface charging measurement session; (b) chemically resolved electrical measurement session; and (c) angular resolved spectroscopic measurement session.

In some embodiments, the first and second spectroscopic data are obtained by carrying out XPS measurements while varying the electrical condition of the sample e.g. by using an electron flood gun.

As indicated above the intensity changes data may be obtained using electrical measurements (e.g. CSC), or using angular-based measurements (ARXPS) or ARES (Angular Resolved Electron Spectrometer) type measurement session including at least one, take-off angles to obtain a complete angular resolved spectroscopy of the sample. As for the second spectroscopic data (spectral shift and shape distortion), it utilizes the electrical measurements, and it comprises spatial distribution of the chemical element with a certain spatial resolution, while the measured data resulted from the analysis of the first and second data comprises spatial distribution of a chemical element with a higher spatial resolution.

According to another broad aspect of the present invention, there is also provided a method for examining a sample. The method comprises: applying first and second XPS based measurements to the sample at different electrical conditions, respectively, of the sample, thereby obtaining first and second spectroscopic data from the sample indicative of respectively a change in amplitude of a photoelectron signal from the sample, spectral line shift and shape distortions; analyzing the first and second spectroscopic data and generating measured data indicative of a material compositional profile of the sample and is spatial distribution of chemical elements in the sample along a direction across the sample, the measured data being thereby indicative of compositional and quantitative concentration variations (inhomogeneity) of a predetermined chemical element in the sample along the direction across the sample.

According to yet another broad aspect of the present invention, there is also provided a system for examining a sample. The system comprises: an excitation source producing high energy radiation to cause emission of internal charged particles from the sample; an electronic device associated with the sample for affecting an electrical condition of the sample; an analyzer unit including a charged particles' spectrometer and a detector unit connected to the output of the spectrometer; and a control system configured and operable to operate the electronic device to vary electrical condition of the sample and to receive measured data from the analyzer unit and determine changes in a signal intensity data from the sample, spectral line shift and spectral line shape distortion, thereby identifying spatial distribution of chemical elements in the sample along a direction across the sample.

The electronic device may comprise at least one voltage supplier, connected to a back contact of the sample and configured and operable for applying a voltage across the sample, and preferably also comprises a source of (low-energy) charged particles for charging the sample at a given surface charge state. The source of low-energy charged particles may be an electron flood gun. In some embodiments, the control system is configured and operable to control the operation of the source of (low-energy) charged particles to appropriately vary the (low-energy) charged particle flux and the bias voltage values in a desired manner during the measurements.

The control system may comprise a memory utility for storing the first and second data.

In some embodiments, the excitation source and the analyzer form an XPS measuring unit for obtaining spectroscopic data from the sample.

The excitation source may be configured and operable to produce X-ray beam impinging on a surface region of the sample, resulting in emission of photoelectrons. The given surface charge state of the sample may be an uncharged state.

In some embodiments, the analyzer comprises an ARES type measurement unit.

In some embodiments, the detector unit comprises at least two detection components, such that different take-off angles can be detected simultaneously.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
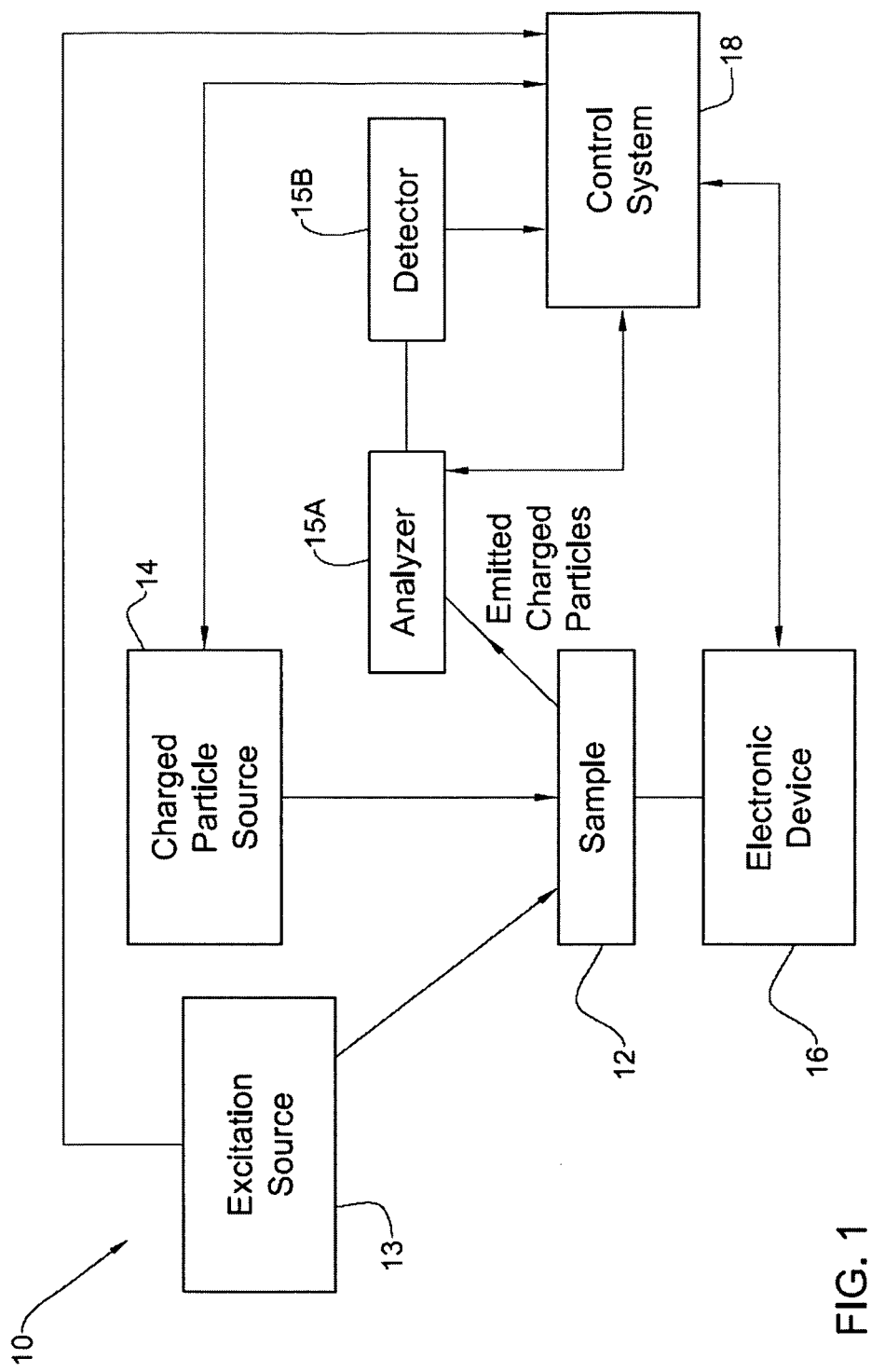
FIG. 1 is a block diagram illustrating the main elements of the system of the present invention.

Referring to FIG. 1, there is illustrated, by way of a block diagram, a system 10 according to the invention for examining a sample 12. The latter is typically a multi-layer structure composed of several components of different materials, and may include small structures ranging from the nanoscale up to micrometer and larger scales. For example, the sample includes a silicon oxynitride structure.

The system 10 is configured and operable for determining distribution of a certain material across the structure (through the structure) with high resolution, which may be of the order of about 1-2 Å for example in SiON systems. In other words, the system generates data indicative of inhomogeneity of the compositional profile and spatial distribution for a chemical element in the sample along a direction perpendicular to a surface of the sample. This is implemented by obtaining first and second spectroscopic data from the sample. The first spectroscopic data include a signal intensity data (i.e. the integral intensity of any given photoelectron signal) from the sample and is indicative of a material compositional profile of the sample. The second spectroscopic data corresponds to spectral line shifts and shape distortion, being thus indicative of spatial distribution of chemical elements across the sample. Analyzes of the first and second spectroscopic data allows for determining the compositional profile and spatial distribution for a chemical element in a direction across the sample. It should be understood that the line intensity change, and the line shift and shape-distortion are two independent orthogonal spectral effects (occurring along two different axes of the spectrum in any depth profile). Therefore, the analysis of these two spectral data improves considerably the accuracy and the reliability of the system and method of the present invention.

The system 10 includes an excitation source 13 producing high energy radiation (e.g. a source of monochromatic electromagnetic radiation such as X-ray beam, and/or an e-beam source, and/or an ion beam source) to cause emission of internal charged particles from the sample. Further provided in the system is a source of low-energy charged particles 14, e.g. electron beam source (preferably, yet not limited to, up to 10 eV in kinetic energy) or a source of slow ions (e.g., $He^+$-beam); an analyzer (including a charged particles' spectrometer 15A, and a detector unit 15B connected to the output of the spectrometer 15A); and an electronic device 16. The latter includes at least one voltage supplier, connected to a back contact of the sample (and may also include a variable external resistor), and includes an electric current measure (e.g. ampermeter). The excitation source 13, analyzer 15A, 15B may for example be constituted by an XPS measuring unit, the construction and operation of which are known per se.

Further provided in the system 10 is a control system 18 being connectable to the elements of the system 10. The control system 18 is typically a computerized system, including inter alia a memory utility, a data processing and analyzing utility, a setting utility (for operating the charged particles' source 14, the electronic device 16, and the voltage supplier); and a suitable interface utility.

An X-ray beam produced by the source 13 impinges on the surface region of the sample 12, resulting in the emission of photoelectrons. Photoelectrons emerging from a selected portion of the sample region are directed into the analyzer 15A and the output of the analyzer is received at the detector unit 15B that generates data indicative of the detected photoelectrons. Such data taken at a given surface charge state of the sample (e.g. uncharged sample) present the first spectroscopic data including an intensity of a photoelectron signal from the sample. This data is indicative of a material compositional profile of the sample. This data in combination with that of at least one additional measurement taken in at least one different surface charge state of the sample, obtained by charging the sample by the charged particle source 14, allows to obtain second spectroscopic data (by applying appropriate spectral analysis). The second spectroscopic data includes spectral line distortions, and is thus indicative of spatial distribution of chemical elements in the sample along a direction across the sample. The first and second data are stored in the memory utility. The control system (its setting utility) controls the operation of the electron flood gun 14 to appropriately vary the flood gun flux and the bias voltage values in a desired manner during the measurements.

The following is a specific but not limiting example of a method according to the invention.

A measurement session in two different electrical conditions of the sample according to the teachings of the present invention is performed. Corresponding measured data (second spectroscopic data) may include various spectral lines (i.e. elements, j) at two (or more) electrical conditions, labeled here as original (Oj) and distorted (Dj). Then, a distortion function, $\Delta(z)$, is determined, which describes the electrostatic potential vs depth (z), from the results of the CSC-based measurements. In the simplest case, $\Delta(z)$ is linear, with a constant field (E) magnitude: $\Delta(z)=\Delta_0+Ez$.

An ARES type measurement session is performed, e.g. an XPS or Auger spectroscopy (this is an optional measurement, because similar information can be obtained from the electrical CSC-based measurement of the present invention). The results of such measurement session may include at least one, and possibly a plurality of take-off angles to obtain a complete angular resolved spectroscopy of the sample.

For each chemical element (j), a guess depth profile function (Pj) is determined, such that $$\sum_j Pj(z) = 1.$$

Initially, a guess function can be used, based on the following: (1) an arbitrarily chosen profile, e.g. based on independent information; (2) a first order analysis of the CSC data (i.e. by comparing the peak shift of various lines); (3) deconvolution of the CSC results (see example below). Pj is a function of depth (z), and it is specified for each of the relevant elements (j) observed in the electron spectroscopy (ES) data. Being distribution functions, all Pj are real and positive.

Attenuated profile functions (AjPj) are computed for the functions Pj. Here, Aj(z) is the attenuation factor of spectral line j. In the simplest case, it is an exponential function of the depth z.

A convolution function is computed for each element j: AjPj*Oj=Dj'. Namely, the attenuated profile function is convoluted with the original CSC-based measurement results (Oj). The calculated convolution results Dj' are compared with the distorted CSC-based spectra (measured Dj), and a quantitative measure of fitness, F1, is derived.

The measured spectral lines or measured spectrums are used to extract the line intensities data (Ij) from the spectrum.

Simulated line intensities (SIj) are computed from the attenuated profile functions. This is frequently calculated with the expression:

$$SIj = \frac{1}{\lambda_j} \int Aj(z)Pj(z)dz,$$

where $\lambda j$ are attenuation parameters.

The computed (simulated) intensities, SIj, are compared with the experimental intensities, Ij, and a quantitative measure of fitness, F2, is derived.

Parameters of the profile functions, Pj, are varied in a desired amount.

Then, the above steps starting from determination of the depth profile function (Pj), are repeated in an iterative manner, to obtain optimal fit for both F1 and F2, and optionally also quantitative measure of fitness Fa corresponding to a condition that $$\sum_j Pj(z) = 1.)$$

It should be emphasized that the above procedure can be extended to data recorded at more than a single takeoff angle and/or to include a full angular analysis of intensities. Accordingly, the measuring instrument may include more than a single detection component, such that different takeoff angles can be detected simultaneously.

Further, it should be emphasized that both "undistorted" and "distorted" measurements may be conducted in only a single common take-off angle, thus to enabling to concurrently obtain "intensity" and "energy" (compositional profile dependent) functions.

It should further be noted that the technique described herein may be extended to include additional fit parameters (F3, F4, etc.) extracted from simulations with the Tougaard's method for peak to background analysis, and/or to include variations in the distortion function.

The following are some experimental results of using the technique of the present invention.

Figure 2A:
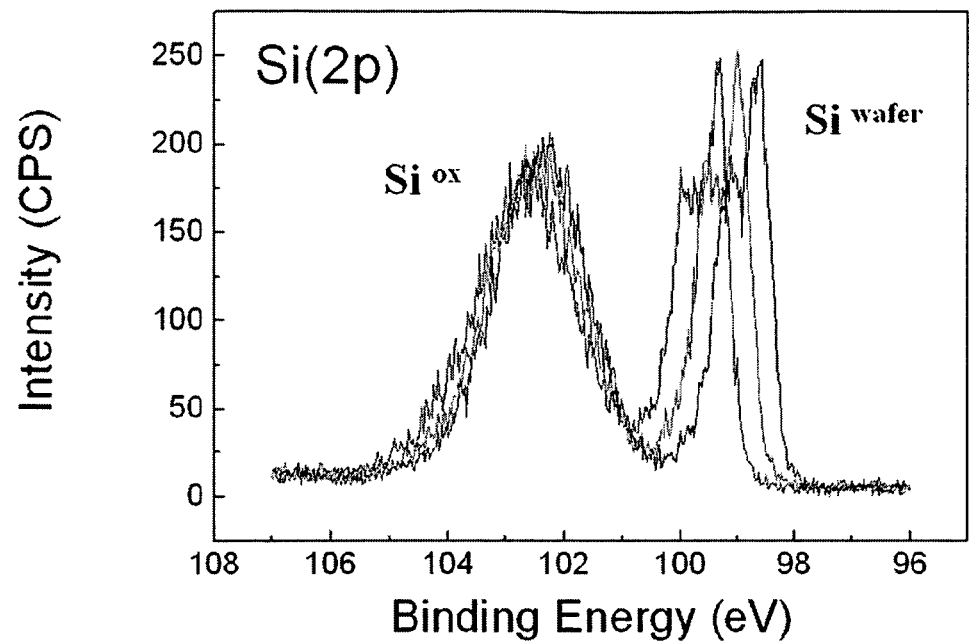
FIG. 2A represents selected Si 2p spectra under VB changes by steps of 0.4 V.

Reference is made to FIG. 2A illustrating three spectra corresponding to three different sample bias ($V_B$) values under fixed electron flood gun (eFG) conditions (2.5 V; 1.85 A) of a thin SiON layer (in this example having a thickness of 36 Å). The differences in peak shifts reflect potential gradients created across the sample structure. Clear line shifts of the substrate ($Si^{wafer}$) peak are observed, whereas the oxidized Si ($Si^{ox}$) peak shifts are considerably smaller. The actual potential values developing across the measured structure are extracted from these line shifts ($\Delta E$), corrected for the trivial shifts under $V_B$ changes, i.e., $V=\Delta E/e+\Delta VB$, where e is the electron charge, and zero potential is arbitrarily determined at the first measurement, i.e., at the step of minimal current.

The oxynitride films were prepared on p-type ($10^{15}$ cm$^{-3}$ boron) Si (100), growing first thermal $SiO_2$ layers on precleaned substrates, and subsequently applying rapid thermal nitridation under pure $NH_3$ atmosphere at 1050° C. Different N concentrations were obtained via temperature control in a range of ±10° C.

Measurements were performed on a Kratos AXIS-HS instrument using a monochromatic Al (K$\alpha$) source. The angular width of the XPS detection system is about ±15°. Complementary measurements were performed in an electrostatic mode with angular acceptance of about ±2° only. Samples were connected to the sample holder by a double-sided carbon tape after scratching mechanically the backside of the sample. Electrical input signals were applied with (1) an electron flood gun (eFG), controlled via filament current and two bias voltages and (2) a Keithley 487 electrometer for biasing the back contact of the sample.

ToF-SIMS was conducted with a Physical Electronics TRIFT II instrument using a dual beam-phased mode, with a 15 KeV Ga+ ion beam at the analysis phase and a 250-500 eV Cs+ ion beam at the sputtering phase. Implant standards in $SiO_2$ and Si were used in the quantification of the nitrogen profiles. For the interface region, a relative sensitivity factor was applied as a function of the Si intensity signal [7].

Figure 2B:
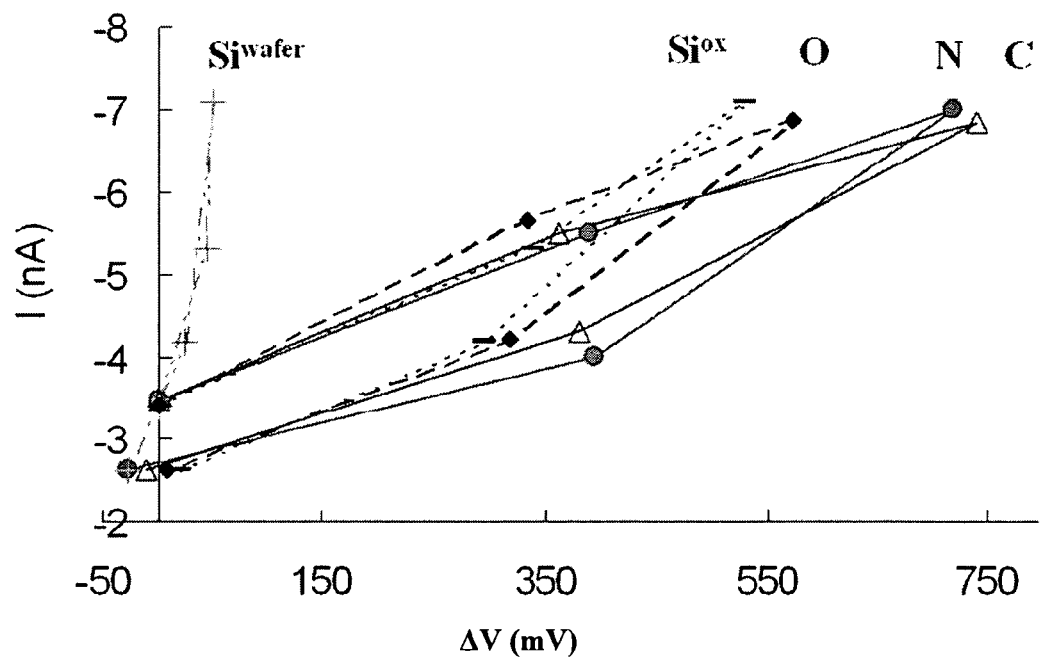
FIG. 2B represents the corresponding I-V characteristics under stepwise variations in VB (−0.4 V, 0 V, +0.4 V, 0 V, 0.4 V) and fixed eFG parameters.

Reference is made to FIG. 2B illustrating the corresponding I-V characteristics. The experiment is conducted by first increasing $V_B$ in steps of 0.4V and then lowering it back by the same increments. All the curves exhibit minor hysteresis in potentials and a more pronounced current hysteresis, originating in capacitive effects, which have a minor impact on the present analysis. The carbon (a top marker of the structure) and the substrate (a bottom marker, $Si^{wafer}$) present the two extremes in potential variations, as expected from their vertical positions. The initial (first measurement) line positions are chosen arbitrarily as zero potential points. Interestingly, differences evolve also between N and both O and $Si^{ox}$, suggesting an inhomogeneous composition with N enrichment at the top of the layer.

Figure 3:
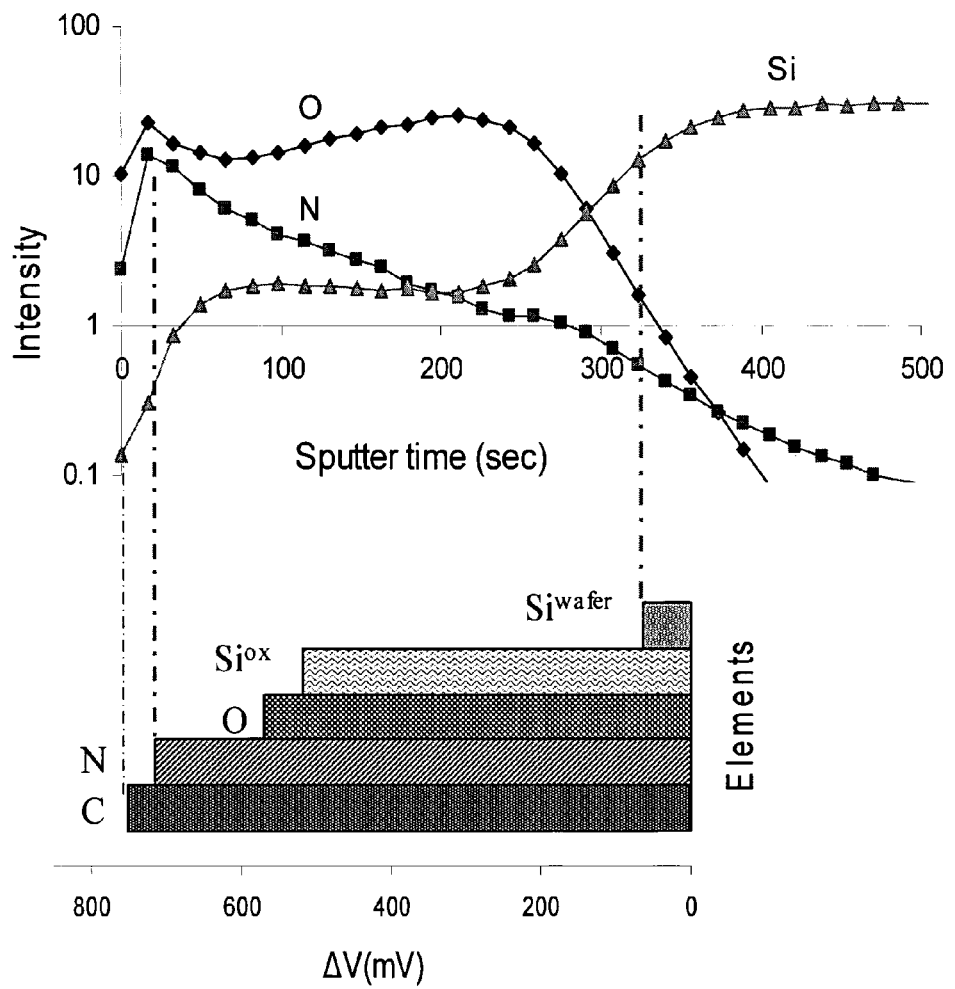
FIG. 3 represents comparison of ToF-SIMS (top) and CSC (bottom) derived profiles of a 36 Å thick SiON layer on Si.
Figure 4:
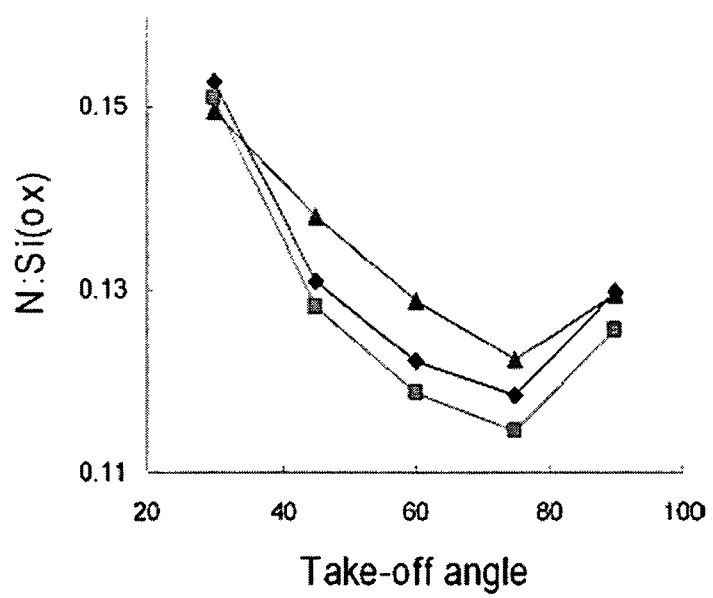
FIG. 4 represents angle dependent data (ARXPS data), showing the intensity ratio N:Si(ox) with calculated ratios based on ToF-SIMS profiles.
Figure 5:
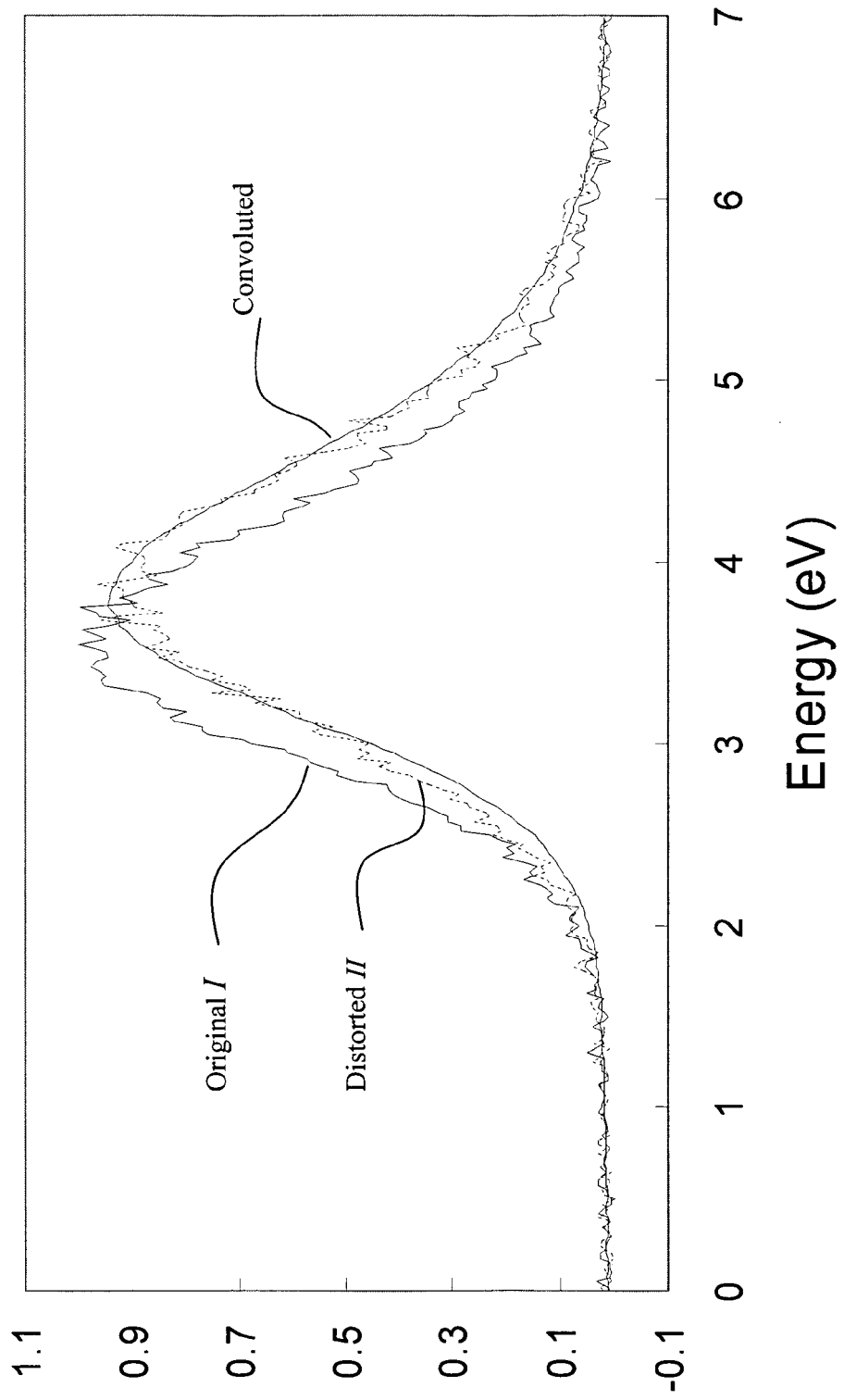
FIG. 5 is a frozen step in the line shape analysis; the original spectrum I is convoluted with a trial profile function the convolution result is to be compared quantitatively with the distorted spectrum H.

Reference is made to FIGS. 3 to 5 showing a specific but not limiting example of the technique of the present invention. This example includes XPS-based analysis, wherein the first and second spectroscopic data is obtained by carrying out CSC-based and ARES-based measurements session of a 36 Å thick SiON on a Si wafer. A test (destructive) profile with ToF-SIMS is used for comparison. Comparison between CSC-based measurement of peak shifts and ToF-SIMS profiling data is shown in FIG. 3. Both techniques show the same gross features, and in particular, the N-enrichment at the surface. Both O and N are probed via Si-containing fragments of comparable yields, $SiO_3$ and $SiN$, subsequently divided by the Si signal to get the net elemental curves.

A linear distortion function is used here for the second spectroscopic data: $\Delta(z)=\Delta_o+Ez$.

Apparently, the peak shift analysis provides a quick indication for the gross profile features: (1) the existence of top C contamination and bottom Si wafer; (2) the N-enrichment at the top of the oxide layer; (3) a small difference between the O and $Si^{ox}$ distribution functions, with some enhanced O amount at the surface. O-surface enrichment is further resolved by ToF-SIMS, attributed to surface contamination (e.g., OH groups). Accordingly, a small difference between O and Siox is observed in the CSC data (FIG. 3, bottom), and also in line shape modifications. A relatively small N enrichment is resolved at the inner interface (around 280 s in the ToF-SIMS profile, not observed by CSC), which is driven chemically by the large number of interface dangling bonds. The Siox and O profiles represent intermixed, non-identical distributions, while their data points in FIG. 3 correspond to peak shifts, namely, to weighted average values.

It should be noted that as clearly shown, peak shifts do not reveal fine details; the slab thickness information is expressed in line broadening, and fine distribution details affect the detailed line shape analyzed by the method of the present invention.

Reference is made to FIG. 4, top curve, presenting experimental ARXPS data indicative of the elemental concentration profiles: the $N:Si^{ox}$ intensity ratio. The non-monotonic angular dependence obtained here exemplifies cases where the data interpretation is difficult. Consistency of the data is however confirmed by comparing with the calculated curve, obtained by introducing attenuation factors to the independently derived ToF-SIMS profile, see simulated ARES, FIG. 4, bottom curve.

Experimental data is presented by the curve having triangle points, a simulated (calculated) full layer is provided for comparison, by the curve having diamond points, a simulated (calculated) partial layer is provided for comparison, by the curve having square points, based on the independently derived ToF-SIMS profile.

The ARXPS is applied as a second independent technique. The angle dependent $N/Si^{ox}$ intensity ratios probed in the electrostatic mode, manifest a minimum at $\theta=75°$. Such non-monotonic angle dependence may pose questions on the above-indicated N surface enrichment. However, using the ToF SIMS N and Si profiles, and applying a standard attenuation correction for their XPS signal, it is straightforwardly shown that the expected ARXPS should indeed consist of a minimum around 75° (see FIG. 4 intermediate curve with diamond points). Energy dependence of the electron attenuation length is accounted for, using 25.3 and 20.7 Å for Si and N, respectively. Previous simulations suggested a similar minimum when a second N-enriched region was introduced at the interface with the substrate. Here, however, the inner N-enriched layer contributes <2% of the N signal, with no significant effect on the XPS data. The bottom curve (square points) in FIG. 4 is calculated with the top part only of the oxide layer, down to the depth of 210 s sputtering, thus excluding the inner interface and yet the unusual angular dependence is retained. Thus, this specific example demonstrates a general difficulty in obtaining conclusive interpretation of ARXPS in nontrivial structures.

Compared to ToF-SIMS and ARXPS, the method of the present invention proposes several important advantages. It is nondestructive, relatively quick and easy for operation, and can, in principle, achieve excellent depth resolution in dielectric systems consisting of sufficient chemical contrast, down to the atomic scale. The accuracy in line-shift determination is typically around 20-50 meV, frequently even <10 meV, which corresponds here to depth resolution on the order of 1-2 Å. On the other hand, as indeed observed in the O and $Si^{ox}$ signals, potential gradients across layers of finite thicknesses impose line shape distortions which can, in general, be quite large. In the present case, the experimental error for O and $Si^{ox}$ increases to about 100 meV (i.e. ~5 Å depth resolution). Still, the two N-enriched layers should be resolved easily (about 500 meV split for about 25 Å spatial separation), with a clear advantage over ARXPS, provided that the inner N concentration is higher. It was, in fact, hardly observable by the ToF-SIMS as well. Notably, the C and N lines did not show observable line shape distortions, indicating small thickness of the corresponding layers; and in particular, less than 1 nm for the top N-enriched slab.

To quantitatively inspect the effects associated with fine distribution details, an approximately constant internal electric field is assumed, such that the z-axis is linearly projected on the potential scale. This assumption is justified here since the dielectric constant of SiON (here, about 4% N) is very close to that of $SiO_2$. Using the SIMS-derived profile (FIG. 3), a depth dependent (attenuated) signal is calculated and this function is convoluted with the initial line shape. FIG. 5 presents two experimental O lines: initial (I) and electrically distorted (D). The figure shows the second stage treatment via line shape analysis of the O (1s) line. The initial (original) spectrum I is convoluted with a trial profile function and the resultant calculated spectrum can be compared with the measured distorted spectrum (II). A measure of fitness is to be derived from the comparison between the two latter spectra. The profile function used in this specific example is the concentration profile derived by ToF-SIMS corrected for attenuation (FIG. 3, top). The convolution result is to be compared quantitatively with the distorted spectrum II.

The computed convolution of the former with the attenuated profile function is therefore shown, yielding close agreement with the experimental (distorted) spectrum. A similar agreement is obtained for the $Si^{ox}$ distortion. Slight deviations are observed in both cases, partially due to the above-mentioned inaccuracies in the Si SIMS profile, and also due to the fact that the constant field assumption cannot be extended to the surface contamination region.

Therefore, the inventor of the present invention has found that when the sensitivity of the line shift based measurements is limited, electron attenuation considerations become useful. As indicated above, conventional depth profiling techniques exploit "spectral peak-shift based measurements" or intensity change analyses (possibly using angular-resolved measurements) that exploit intensity data. In some cases, these measurements are not sensitive enough to the composition profile, or frequently, unable to distinguish between plural profiles that would give the same data, and thus combination of the spectral shift and shape distortion data (i.e. attenuation) with the signal intensity data provides for meaningful improved analysis. Combining the line intensity quantification and line shift and shape analysis is particularly powerful since these are two orthogonal spectral effects (intensity versus energy) of any depth profile, which can be used complementarily to improve reliability and versatility of the method.

The invention claimed is:

1. A method for examining a sample, the method comprising:

obtaining spectroscopic data from the sample having multiple materials while under at least two different electrical conditions of the sample, said spectroscopic data comprising a first spectroscopic data being quantified-type data indicative of an amplitude change of a photoelectron signal from the sample with a change in the electrical condition of the sample and being thus indicative of a material compositional profile of the sample along a direction perpendicular to a surface of the sample; and second spectroscopic data being indicative of change in spectral line shifts and shape distortion with a change in the electrical condition of the sample and thus indicative of spatial distribution of chemical elements in the sample along said direction;

combining the results of the two spectroscopic data; and generating measured data of the compositional profile and spatial distribution being indicative of inhomogeneity of the compositional profile and spatial distribution for at least one chemical element in the sample along said direction.

2. The method of claim 1, wherein said obtaining of the spectroscopic data comprises measuring the intensity of the photoelectron signal from the sample as a function of the electrical condition of the sample, the intensity change spectroscopic data being a function of a material composition of the sample, and said second spectroscopic data comprising the change in the spectral position and shape is indicative of attenuation of the photoelectron signal from the sample.

3. The method of claim 1, wherein said obtaining of the spectroscopic data comprises:

(i) exciting the sample with high-energy radiation to cause emission of internal charged particles from the sample;

(ii) varying certain electrical condition of the sample, (iii) during the variation of the electrical condition, measuring the emitted charged particles versus their energy.

4. The method of claim 3, wherein said varying of the electrical condition of the sample comprises at least one of the following: supplying electrical power to a circuit formed by the sample and any added component connected to a back contact; irradiating the sample by charged particles, subjecting the sample to an external field, and irradiating a sample by electromagnetic radiation.

5. The method of claim 1, wherein said obtaining of the spectroscopic data comprises carrying out at least one of the following: controlled surface charging (CSC) measurement session and chemically resolved electrical measurement (CREM) session.

6. The method of claim 5, comprising further carrying out angular resolved spectroscopic measurement session.

7. The method of claim 1, wherein said sample is least one of a heterostructure and a multi-layer structure.

8. The method of claim 1, wherein said sample comprises a silicon oxynitride structure, said measured data being indicative of the inhomogeneity of nitrogen across the structure.

9. The method of claim 1, wherein the spectroscopic data comprises spatial distribution of the chemical element with a certain spatial resolution, analysis of said spectroscopic data provides spatial distribution of said chemical element with a higher spatial resolution.

10. The method of claim 1, comprises fitting the spectroscopic data to corresponding theoretical data wherein said fitting comprising:

(a) obtaining a guess function having parameters indicative of a desired compositional profile and spatial distribution for at least one chemical element in the sample along a direction through the sample;

(b) convoluting said guess function with said spectroscopic data obtained under a certain surface charge state of the sample and generating a convolution result for each chemical element;

(c) comparing said convolution result with said spectroscopic data obtained under a different surface charge state of the sample, and obtaining a first quantitative measure of fitness;

(d) comparing the convoluted result with the spectroscopic data of the photoelectron signal;

repeating steps (b)-(d) while varying said parameters until an optimal value of said first quantitative measure of fitness is obtained.

11. The method of claim 10, comprising processing said guess function with an attenuation function of each spectral line as function of direction through the sample to obtain attenuated profile functions.

12. The method of claim 10, comprising:

extracting line intensities from said spectroscopic data;

(e) processing said guess function to obtain simulated line intensities of the photoelectron signal;

(f) comparing said simulated line intensities with said line intensities and obtaining a second quantitative measure of fitness;

(g) repeating the steps (b)-(f) while varying the parameters of said guess function until optimal values of said first and second quantitative measure of fitness is obtained.

13. The method of claim 10, wherein said obtaining of said guess function comprises at least one of the following: determining an arbitrarily chosen profile; analyzing said spectroscopic data; and deconvoluting said spectroscopic data.

14. The method of claim 1, comprising: processing said spectroscopic data to determine a distortion function indicative of an electrostatic potential as a function of a direction through the sample.

* * * * *